(12) United States Patent
Bernhard et al.

(10) Patent No.: US 9,313,587 B2
(45) Date of Patent: Apr. 12, 2016

(54) HEARING AID COMPRISING AN INTRA-COCHLEAR ACTUATOR

(75) Inventors: Hans Bernhard, Koeniz (CH); Volkmar Hamacher, Hannover (DE)

(73) Assignee: Advanced Bionics AG, Stäfa (CH)

( * ) Notice: Subject to any disclaimer, the term of this patent is extended or adjusted under 35 U.S.C. 154(b) by 104 days.

(21) Appl. No.: 13/576,288

(22) PCT Filed: Feb. 12, 2010

(86) PCT No.: PCT/EP2010/051819
§ 371 (c)(1),
(2), (4) Date: Jul. 31, 2012

(87) PCT Pub. No.: WO2011/098144
PCT Pub. Date: Aug. 18, 2011

(65) Prior Publication Data
US 2012/0303097 A1  Nov. 29, 2012

(51) Int. Cl.
*A61N 1/372* (2006.01)
*H04R 25/00* (2006.01)
*A61N 1/05* (2006.01)
*A61N 1/36* (2006.01)

(52) U.S. Cl.
CPC ............ *H04R 25/606* (2013.01); *A61N 1/0541* (2013.01); *A61N 1/0558* (2013.01); *A61N 1/36032* (2013.01); *H04R 2225/023* (2013.01); *H04R 2225/67* (2013.01)

(58) Field of Classification Search
CPC ............ A61N 1/36032; A61N 1/0541; A61N 1/0558; H04R 25/00; H04R 25/60; H04R 25/606; H04R 2225/67; H04R 2225/023
USPC ......................................... 607/55–57; 600/25
See application file for complete search history.

(56) References Cited

U.S. PATENT DOCUMENTS

| | | | | |
|---|---|---|---|---|
| 5,729,077 A | * | 3/1998 | Newnham | H02N 2/043 310/328 |
| 6,190,305 B1 | * | 2/2001 | Ball | H04R 11/02 600/25 |
| 6,549,814 B1 | | 4/2003 | Strutz et al. | |
| 6,565,503 B2 | | 5/2003 | Leysieffer et al. | |
| 6,629,922 B1 | * | 10/2003 | Puria | H04R 25/606 381/312 |
| 7,082,332 B2 | * | 7/2006 | Blamey et al. | 607/57 |

(Continued)

FOREIGN PATENT DOCUMENTS

| | | |
|---|---|---|
| DE | 42 21 866 A1 | 1/1994 |
| DE | 10 2007 026 631 A1 | 12/2008 |

(Continued)

*Primary Examiner* — Michael Kahelin
*Assistant Examiner* — Minh Duc Pham
(74) *Attorney, Agent, or Firm* — Roberts Mlotkowski Safran & Cole, PC; David S. Safran

(57) ABSTRACT

An at least partially implantable hearing aid has an input transducer (26) for capturing audio signals from ambient sound, an audio signal processing unit (32) for processing the captured audio signals, an actuator (20) for stimulating a patient's hearing, and a driver unit (44) for driving the actuator. The actuator has a rigid housing (64) closed on at least one side by a vibration diaphragm (66) that is driven by a piezoelectric transducer (68, 88). The housing is designed to float in the cochlea in direct contact with the cochlear liquids in order to couple vibration energy from the diaphragm directly into the cochlear liquids.

26 Claims, 4 Drawing Sheets

(56) References Cited

U.S. PATENT DOCUMENTS

| | | |
|---|---|---|
| 7,289,639 B2 | 10/2007 | Abel et al. |
| 7,580,754 B2 | 8/2009 | Zhang et al. |
| 7,618,450 B2 | 11/2009 | Zarowski et al. |
| 2001/0049466 A1 | 12/2001 | Leysieffer et al. |
| 2006/0264897 A1* | 11/2006 | Lobl ................. A61M 39/0208 604/506 |
| 2009/0240099 A1* | 9/2009 | Conn ................... A61N 1/0541 600/25 |
| 2010/0324355 A1* | 12/2010 | Spitaels ............... H04R 25/606 600/25 |

FOREIGN PATENT DOCUMENTS

| | | |
|---|---|---|
| EP | 1 145 733 A2 | 10/2001 |
| WO | 03/063542 A2 | 7/2003 |
| WO | 2008/077943 A2 | 7/2008 |

* cited by examiner

HEARING AID COMPRISING AN INTRA-COCHLEAR ACTUATOR

BACKGROUND OF THE INVENTION

1. Field of the Invention

The present invention relates to an at least partially implantable hearing aid and a corresponding method for providing hearing assistance to a patient.

2. Description of Related Art

Implantable middle ear hearing devices (IMEHD) are offered for people with special hearing losses or special medical indications which cannot be treated with conventional electro-acoustic hearing aids. Typical indications for IMEHDs are radical middle ear cavities, atresia and otosclerosis (especially in combination with sensorineural hearing loss) and chronic infects or allergies of the ear canal.

All IMEHDs have in common that they bridge the non-functioning sound path of the middle ear ossicles by directly mechanically stimulating the cochlear. For this stimulation, various types of actuators have been proposed (e.g., piezo-electric or electro-magnetic) and several are available in certified medical products. All of these actuators have in common that they are placed somewhere in the middle ear cavity. In order to deliver the sound vibration to the cochlear fluids, they are coupled, in most cases, either (a) to the ossicular chain or (b) to the Round Window, or (c) to a piston placed in a small hole drilled in the cochlear in or close to the stapes footplate. Most of these actuator principles need a rigid fixation of the actuator housing on the bone.

For people suffering from deafness or partial deafness, Cochlear Implants (CI) are offered. These devices bypass the outer and the middle ear and stimulate the auditory nerve electrically with an electrode-chain inserted in the cochlea. For people with residual hearing, mostly in the low frequency range, it was shown that, in addition to the electrical stimulation, acoustical stimulation at the frequencies with residual hearing can be beneficial for speech understanding, sound quality and music perception. In today's hybrid systems, the acoustic amplification is realized by integrating an amplifier and a receiver in the CI speech processor and delivering the amplified sound through a tube and a custom-made ear mold to the ear canal as done with conventional hearing aids. The receiver can also be integrated in the ear mold.

Implanting the fixation system of the IMEHD actuator increases the invasiveness and duration of the surgery, which means a higher risk for the patient. However, the major issue is that the precise mechanical adjustment of the actuator in the fixation system and the proper connection to the ossicles, the round window or the piston is the most difficult part of the surgery. Bad fixations or couplings can lead to significant loss of vibration energy and distortions, so that the stimulation arriving at the cochlear fluids is not sufficient to re-establish normal hearing, or even to provide the amplification necessary to compensate a sensorineural hearing loss.

Also, for actuator principles without a fixation system, the risk of inefficient vibration transmission to the inner ear exists. For example, a Floating-Mass-Transducer (FMT) which is directly crimped on the incus needs proper alignment and can become less efficient if the motility of the ossicular chain is reduced. The crimping can also cause inflammatory reactions of the ossicles.

International Patent Application Publication WO 2008/077943 A2 and corresponding U.S. Patent Application Publication 2010/0324355 relate to a hearing aid comprising an actuator having a membrane with a piezoelectric disc-bender arrangement for directly vibrating the inner ear fluids in the cochlear. The membrane is located in a frame structure outside the cochlear, with an open end of the frame being inserted into an opening in the cochlear wall.

International Patent Application Publication WO 03/063542 A2 and corresponding U.S. Pat. No. 7,289,639 relate to a hearing aid comprising an actuator which is a thin disc made of piezo-ceramic material, such as PZT (Lead Zirconate Titanate), which drives, via a fluid-filled tube, a larger diameter disc actuator which contacts the perilymph, wherein the actuator is located outside the cochlea.

U.S. Patent Application Publication 2006/0161255 A1 and corresponding U.S. Pat. No. 7,618,450 B2 relate to a hearing aid comprising a bone-mounted piezoelectric actuator which drives a membrane in contact with the perilymph.

German Patent Application DE 10 2007 026 631 A1 relates to an actuator for a hearing aid inserted into the cochlea, comprising electrodes and electro-mechanical transducers which are implemented as piezoelectric elements.

U.S. Pat. No. 6,565,503 B2 relates to a hearing aid including an actuator to be inserted into the cochlea, which comprises a combination of cochlear implant electrodes and piezoelectric transducers.

U.S. Pat. No. 6,549,814 B1 relates to a hearing aid comprising a cochlear electrode array, which is inserted underneath the spiral ligament of the lateral wall of the cochlear without penetrating into the cochlea. The electrode array may include mechanical transducers implemented as a piezoelectric film.

U.S. Patent Application 2005/0177204 A1 and corresponding U.S. Pat. No. 7,580,754 B2 relate to a piezoelectric pressure sensor which is inserted into the cochlear in direct contact with the perilymph for acting as a microphone.

SUMMARY OF THE INVENTION

It is an object of the invention to provide for an at least partially implantable hearing aid comprising an actuator which may be implanted in a fast and little invasive manner and which provides for reliable and efficient mechanical coupling. It is also an object of the invention to provide for a corresponding method of providing hearing assistance.

According to the invention, these objects are achieved by a hearing aid and a method of providing hearing assistance to a patient as described below.

The invention is beneficial in that, by providing the actuator with a rigid housing closed on at least one side by a vibration diaphragm to be driven by a piezoelectric transducer, wherein the housing is designed for floating in the cochlea in direct contact with the cochlear liquids, the use of a fixation system for the actuator is avoided, thereby enabling faster and less invasive implantation of the actuator; by coupling the vibration energy directly into the cochlear fluids, the risk of losing actuation energy due to weak mechanical coupling of the actuator is eliminated.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
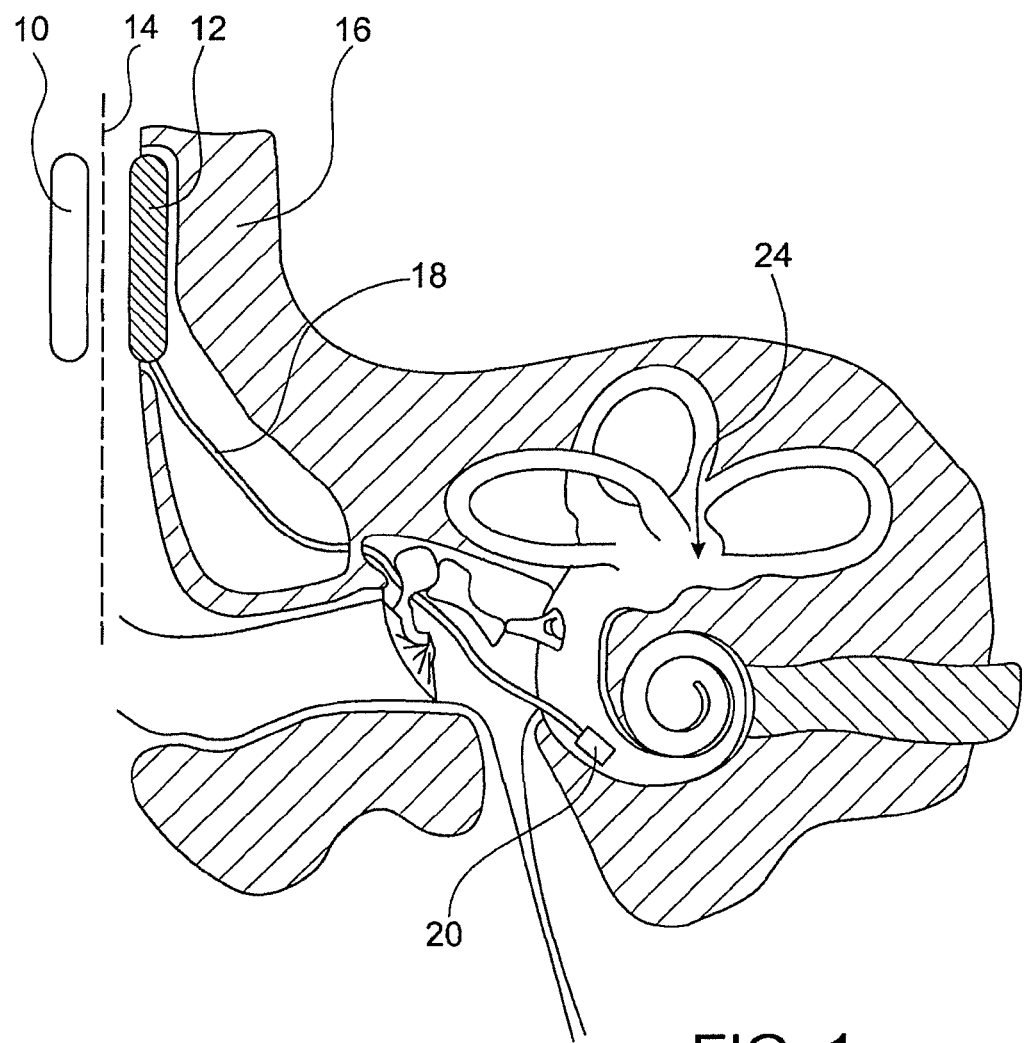
FIG. 1 is a cross-sectional view of an example of a hearing aid according to the invention after implantation.

FIG. 1 shows a cross-sectional view of the mastoid region, the middle ear and the inner ear of a patient after implantation of an example of a hearing aid according to the invention, wherein the hearing aid is shown only schematically. The system comprises an external unit 10, which is worn outside the patient's body at the patient's head and an implantable unit 12 which is implanted under the patient's skin 14, usually in an artificial cavity created in the user's mastoid 16. The implantable unit 12 is connected via a cable assembly 18 to an actuator 20 which is implanted within the cochlear 24. The external unit 10 is fixed at the patient's skin 14 in a position opposite to the implantable unit 12, for example, by magnetic forces created by cooperating fixation magnets provided in the external unit 10 and the implantable unit 12, respectively (these magnets are not shown in FIG. 1).

Figure 2:
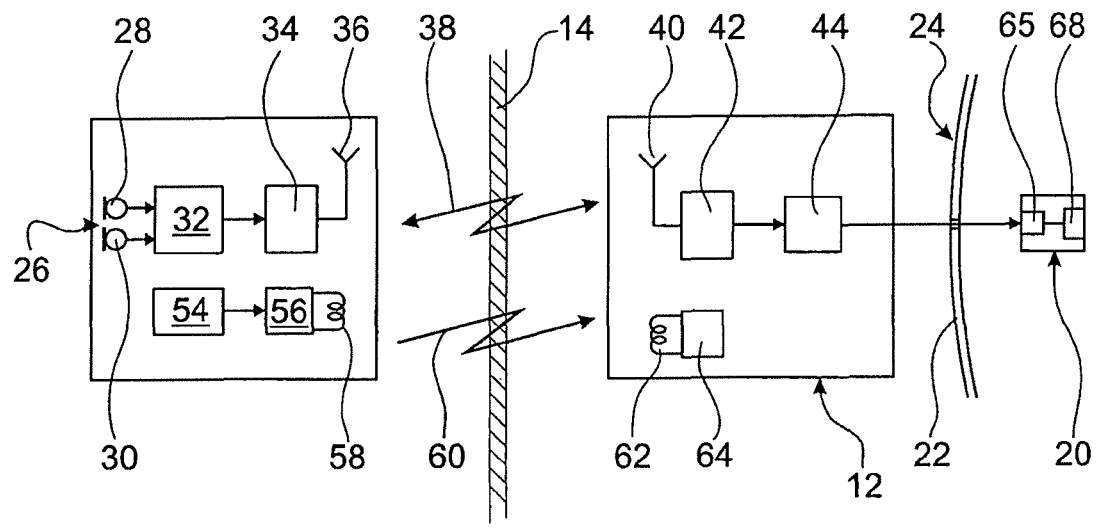
FIG. 2 is a block diagram of the system of FIG. 1.

An example of a block diagram of the system of FIG. 1 is shown in FIG. 2. The external unit 10 includes a microphone arrangement 26 comprising, for example, at least two spaced-apart microphones 28, 30 for capturing audio signals from ambient sound, which audio signals are supplied to an audio signal processing unit 32, wherein they may undergo, for example, acoustic beam forming. The audio signals processed by the audio signal processing unit 32 are supplied to the transmission unit 34 connected to a transmission antenna 36 in order to enable transcutaneous transmission of the processed audio signals via an inductive link 38 to the implantable unit 12 which comprises a receiver antenna 40 connected to a receiver unit 42 for receiving the transmitted audio signals. The received audio signals are supplied to a driver unit 44 which drives the actuator 20.

The external unit 10 comprises a power supply 54, which may be a replaceable or rechargeable battery, a power transmission unit 56 and a power transmission antenna 58 for transmitting power to the implantable unit 12 via a wireless power link 60. The implantable unit 12 comprises a power receiving antenna 62 and a power receiving unit 64 for powering the implanted electronic components with power received via the power link 60. Preferably, the audio signal antennas 36, 40 are separated from the power antennas 58, 62 in order to optimize both the audio signal link 38 and the power link 60. However, if a particularly simple design is desired, the antennas 36 and 58 and the antennas 40 and 62 could be physically formed by a single antenna, respectively.

The actuator 20 is inserted in the scala vestibuli through the oval window or in the scala tympany through the round window or through another access after a cochleostomy. The actuator 20 is designed for floating in the cochlea with direct contact to the cochlear liquids and hence does not need a fixation system (the fact that the actuator 20 is floating in the cochlea does not exclude that the actuator 20 may touch the cochlear wall as long as the actuator 20 is not fixed at or in the cochlea wall; of course, movement of the actuator will be inherently restricted to some extent by the cable assembly 18). This enables a faster, less invasive and consequently less risky surgery procedure, compared to actuators requiring a fixation system. The vibration energy is directly coupled into the cochlear fluids, so that losses of energy due to weak mechanical coupling, as it may occur with actuators fixed at a fixation system in a non-optimal position, can be avoided. Thus, the actuator 20 provides for an acoustical stimulation of the cochlear from "inside".

Figure 3:
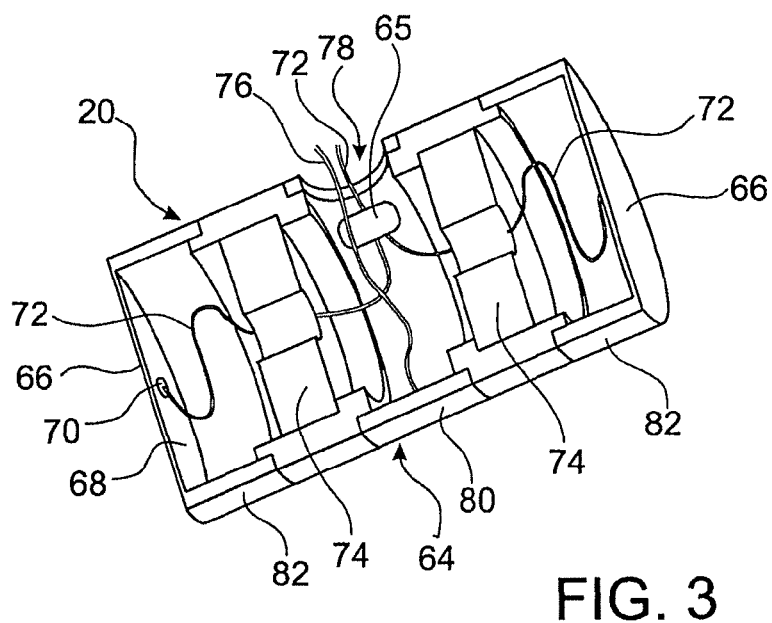
FIG. 3 is a perspective, partially cut away view of an example of an actuator of a hearing aid according to the invention.

In the example of FIG. 3 the actuator 20 comprises a rigid housing 64 which may be made of titanium and which has a cylindrical shape. At both ends, the housing 64 is closed by a diaphragm 66 having a circular shape. The diaphragm 66 is formed by a metal substrate, preferably made of titanium, having a thickness of 2 to 20 µm. An inner side of the metal substrate 66 is provided with a piezoelectric film having a thickness of 1 to 10 µm in order to create a disc-bender configuration. In the configuration shown in FIG. 3, the metal substrate 66 forms a first electrode and second electrode 70 is deposited on the piezoelectric film 68. The electrode 70 is connected to a wire 72 which extends from a hermetic single-pin feed-through section 74 of the housing 64. A second wire 76 is provided for contacting the housing 64 which forms an electrical connection to the metal substrate 66 forming the other electrode. Another branch of the wire 72 is provided for contacting the piezoelectric film 70 of the other diaphragm 66, likewise via a feed-through section 74. The central section 80 of the housing 64 is provided with an opening 78 through which the wires 72, 76 pass into the housing 64. The wires 72, 76 form part of the cable 18.

The various housing sections, i.e., the central section 80, the feed-through sections 74, the end sections 82 and the metal substrates 66, are connected to each other by laser welds. It can be estimated that a volume displacement of about 2.6 nanoliters is necessary for generating a sound pressure equivalent of 125 dB (for example, the ASTM F2504-05 standard correlating the sound pressure in front of the tympanic membrane with the corresponding velocity of the stapes may be applied by integration of the stapes velocity and multiplication with the area of the oval window; the maximum displacement is reached at 500 Hz, and the ASTM standard specifies 0.073 mm/s/Pa as the mean value for the normalized stapes velocity at 500 Hz; the area of the oval window is about 3.2 mm$^2$). For a membrane diameter of 1 mm, such a volume displacement corresponds to a deflection of the membrane of about 10 µm (or 5 µm, if the actuator is provided with two diaphragms, one on each end, as shown in FIG. 3).

Simulations have shown that, for a diaphragm diameter of 1 mm and a titanium diaphragm thickness of 12.5 µm and a piezoelectric film thickness of 8.0 µm, the necessary deflection of 5.0 µm can be obtained with a voltage of 50V, with the piezoelectric film being made of PZT (Lead Zirconate Titanate).

In order to achieve the necessary voltage, the housing 64 may contain a voltage converter (indicated at 65 in FIGS. 1 & 3).

Rather than providing the housing 64 with two single-pin feed-through sections 74, the central section 80 could be designed as a two-wire feed-through.

In view of the geometry of the human cochlea, the housing 64 may have a length of 1 to 3 mm, with a diameter of from 0.5 to 1.5 mm in order to ensure that the housing 64 is floatingly placed within the cochlea, i.e., without permanently touching the inner walls or membranes of the cochlea.

According to the concept shown in FIG. 3, the metallic substrate 66 is used as part of the housing 64 and provides for the necessary mechanical stability, in order to support the piezoelectric film 68. The encapsulation is formed by a hermetic biocompatible titanium housing and the volume of the active part of the actuator, namely the piezoelectric film 68 and the diaphragm 66, is negligible, so that there is enough space for the encapsulation including hermetic feed-throughs for the wires.

Figure 5:
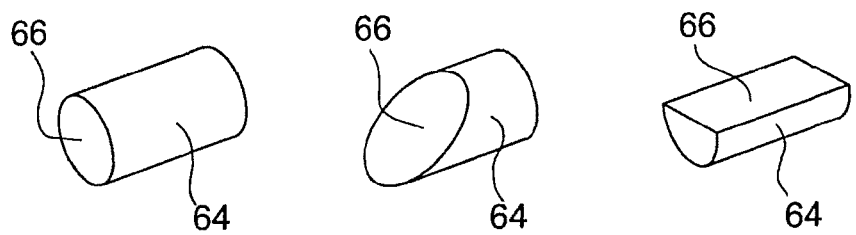
FIG. 5 is a schematic perspective view of three examples of the geometry of the housing of an actuator of a hearing aid according to the invention.
Figure 6:
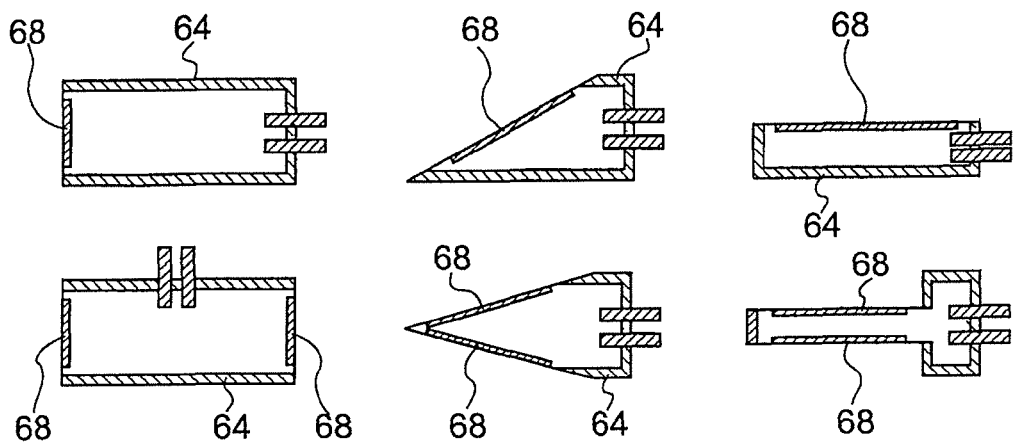
FIG. 6 is a schematic cross-sectional view of several examples of actuators of a hearing aid according to the invention.

As illustrated in FIGS. 5 & 6, also other actuator geometries are possible. In case of a cylindrical housing, the diaphragm may have an elliptic shape, rather than a circular shape, when the end phase of the cylinder is not normal, but slanted with regard to the longitudinal axis of the cylinder. Rather than having a diaphragm at both ends of the cylinder, only one end of the cylinder may be provided with a diaphragm. The diaphragm also may have a rectangular shape, which can be achieved, for example, by cutting away part of the cylinder in the longitudinal direction, with the diaphragm then covering the cut-away surface. As a further alternative, the cylinder may be cut at an angle from both sides.

Figure 4:
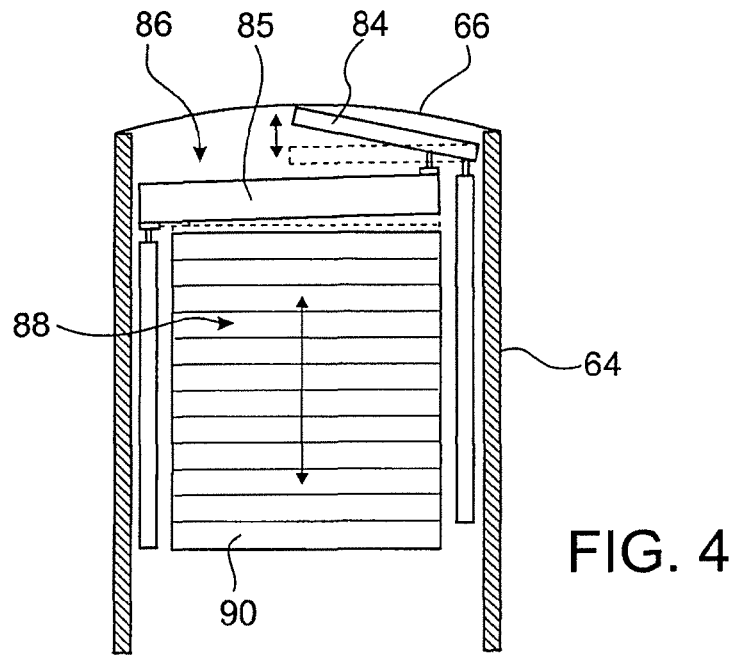
FIG. 4 is a cross-sectional view of an alternative embodiment of an actuator of a hearing aid according to the invention.

An alternative to the disc-bender configuration concept of FIG. 3 is shown in FIG. 4, wherein the diaphragm 66 is not actuated by a piezoelectric film, but rather by a lever element 84 of a lever system 86 which is actuated by a piezoelectric stack 88 formed of a plurality of piezoelectric layers 90 having a thickness of 10 to 100 µm. The lever system 86 and the stack 88 are located within the housing 64. The lever system 86 is for amplifying the deflection provided by the stack 88. Piezoelectric stack actuators are very rigid systems having very high output impedance, i.e., they provide a large force which is more than required for the present application, so that a portion of the force can be "sacrificed" in order to increase the deflection of the membrane by using the lever system 86. The lever system preferably comprises at least two lever stages (in the example of FIG. 4, the lever element 84 forms the second stage, while a lever element 85 forms the first stage), and it may be designed as a single piece cut out of a metallic plate; the articulations are thin flexible beams which interconnect the levers.

In contrast to the example of FIG. 3, the diaphragm 66 does not act as an electrode; rather, both electrodes are provided as part of the piezoelectric stack 88 and are connected to the respective wires via one or more hermetic feed-through sections welded to the main structure of the housing 64.

Figure 7:
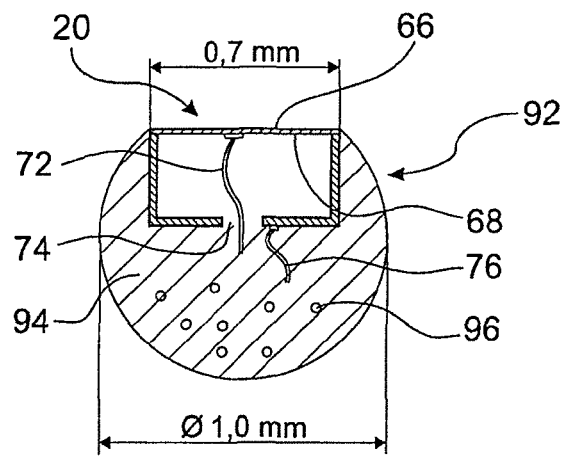
FIG. 7 is a cross-sectional view of an example of an actuator according to the invention when integrated within a cochlear electrode arrangement.
Figure 8:
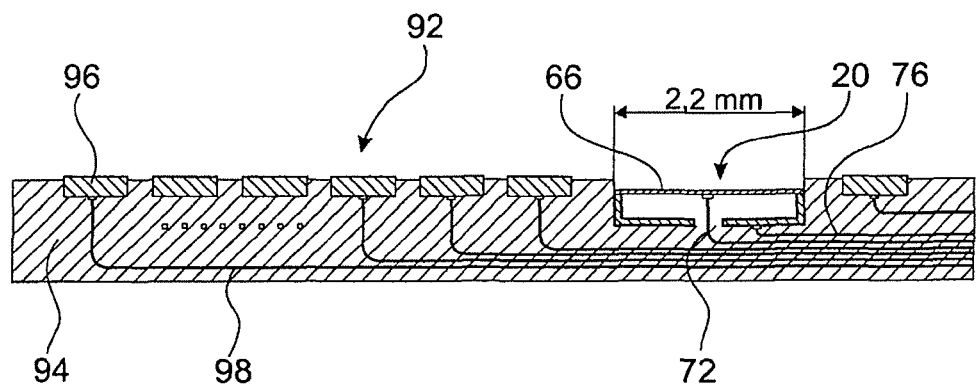
FIG. 8 is a longitudinal sectional view of the cochlear electrode of FIG. 7.

In FIGS. 7 & 8 an example is shown, wherein an actuator of the type shown in FIG. 3, i.e., using the disc bender approach, is integrated within a cochlear implant electrode arrangement 92 which comprises a support structure 94 carrying a plurality of cochlear stimulation electrodes 96, the actuator 20, the wires 88 for the cochlear electrode 96 and the wires 72, 76 of the actuator 20. The support structure 94 may be a silicone carrier.

For example, the diaphragm 66 of the actuator 20 may have a rectangular shape of the size 0.7 mm×2.2 mm, which size would be sufficient for providing for the necessary volume displacement.

According to one embodiment, the actuator housing 64 may be used to act as an electrode for electrical stimulation of the cochlea by applying a suitable voltage to the actuator housing via the wire 76, thereby avoiding a "gap" in the electrode chain at the position of actuator 20 which would be otherwise created. Alternatively, the two electrodes 96 adjacent to the actuator 20 may be excited simultaneously in a manner so as to create a virtual electrode in-between that two electrodes at the position of the actuator 20 (this principle is known as "current steering" in conventional cochlear implant electrodes in order to increase frequency resolution or to bridge defective electrodes.

Also the integration of more than one mechanical actuator 20 is possible, whereby either the total volume displacement could be increased or the actuators 20 could be linked in a way that displacement profiles along the basilar membrane are created which mimic the missing excitation-sharpening function of the damaged outer hair cells.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

The invention claimed is:

1. An at least partially implantable hearing aid comprising an input transducer for capturing audio signals from ambient sound, an audio signal processing unit for processing the captured audio signals, an actuator for stimulating a patient's hearing, and a driver unit for driving the actuator, wherein the actuator comprises a rigid housing closed on at least one side by a vibration diaphragm and a piezoelectric transducer arranged for driving the vibration diaphragm, wherein the housing is flexibly supported in a manner for essentially freely floating in the cochlea in direct contact with the cochlear liquids in order to couple vibration energy from the diaphragm directly into the cochlear liquids, wherein the piezoelectric transducer is provided as a piezoelectric thin film on the diaphragm in a disc bender configuration.

2. The hearing aid of claim 1, wherein the piezoelectric transducer is located within the housing.

3. The hearing aid of claim 2, wherein the housing is made of titanium.

4. The hearing aid of claim 2, wherein the diaphragm has a metal substrate.

5. The hearing aid of claim 4, wherein the metal substrate is made of titanium.

6. The hearing aid of claim 4, wherein the metal substrate is laser-welded to the housing.

7. The hearing aid of claim 2, wherein a voltage converter is located within the housing.

8. The hearing aid of claim 1, wherein the diaphragm has a circular, elliptic or rectangular shape.

9. The hearing aid of claim 8, wherein the housing has a cylindrical shape, with the diaphragm having a circular or elliptic shape and closing at least one end face of the housing, said end face being normal or slanted with regard to a longitudinal axis of the cylinder.

10. The hearing aid of claim 9, wherein both ends of the housing, are closed by a diaphragm.

11. The hearing aid of claim 9, wherein the outer diameter of the housing, is from 0.5 to 1.5 mm.

12. The hearing aid of claim 8, wherein the housing has the shape of a cylinder a side of which was cut away in a longitudinal direction, with the diaphragm covering the cut-away side.

13. The hearing aid of claim 1, wherein the length of the housing is from 1 to 3 mm.

14. The hearing aid of claim 1, wherein the actuator is integrated within a cochlear implant electrode arrangement for electrical and acoustical stimulation of the cochlea.

15. The hearing aid of claim 14, wherein a plurality of actuators are integrated within an electrode arrangement in a manner adapted to create a displacement profile which mimics an excitation-sharpening function of outer hair cells a wearer's ear.

16. The hearing aid of claim 1, wherein the piezoelectric film has a thickness of 1 to 10 μm.

17. The hearing aid of claim 1, wherein the piezoelectric film is made of PZT.

18. The hearing aid of claim 1, wherein the diaphragm has a metal substrate having a thickness from 2 to 20 μm.

19. The hearing aid of claim 18, wherein the metal substrate forms a first electrode and wherein a second electrode is deposited on the piezoelectric film.

20. The hearing aid of claim 19, wherein the actuator is connected by at least two wires, wherein the piezoelectric film and the second electrode are located on an inner side of the diaphragm, with the housing comprising a hermetic single-pin feed through section for connecting the second electrode to one of the wires, and wherein the metal substrate is connected to another one of the wires.

21. The hearing aid of claim 1, wherein the actuator is adapted for being inserted into a scala vestibuli through an oval window or into a scala tympany through a round window or through an artificial window after a cochleostomy.

22. A method for implanting the actuator of the hearing aid of claim 1, comprising the steps of inserting an actuator having a vibration diaphragm into a scala vestibuli through an oval window or into a scala tympany through a round window or through an artificial window after cochleostomy, and arranging the actuator to float in cochlear liquids.

23. A method of providing hearing assistance to a patient, comprising the steps of: capturing audio signals from ambient sound, processing the captured audio signals, and stimulating the patient's hearing by an implanted actuator comprising a rigid housing closed on at least one side by a vibration diaphragm driven by a piezoelectric transducer while the actuator is flexibly supported in a manner for essentially freely floating in a cochlea in direct contact with the cochlear liquids, and coupling vibration energy from the diaphragm directly into the cochlear liquids.

24. The method of claim 23, wherein the actuator is integrated within a cochlear implant electrode arrangement for electrical and acoustical stimulation of the cochlea, and wherein the actuator housing is used to act as an electrode for electrical stimulation of the cochlea by applying a suitable voltage to the actuator housing.

25. The method of claim 23, wherein the actuator is integrated within a cochlear implant electrode arrangement having two electrodes for electrical and acoustical stimulation of the cochlea, and wherein the two electrodes are positioned adjacent to the actuator and are excited simultaneously with the actuator in a manner so as to create a virtual electrode in-between said two electrodes.

26. An at least partially implantable hearing aid comprising an actuator for stimulating a patient's hearing and an implant unit which is adapted for being implanted under a patient's skin, the implant unit comprising a driver unit for driving the actuator, wherein the actuator comprises a rigid housing closed on at least one side by a vibration diaphragm and a piezoelectric transducer arranged for driving the vibration diaphragm, wherein the housing is flexibly supported in a manner for freely floating in the cochlea in direct contact with the cochlear liquids connected only to a cable assembly that connects the actuator to the implant unit in order to couple vibration energy from the diaphragm directly into the cochlear liquids.

* * * * *